United States Patent [19]

Schmidt et al.

[11] Patent Number: 4,994,553

[45] Date of Patent: Feb. 19, 1991

[54] IMMUNOGENIC PEPTIDES OF HUMAN INTERLEUKIN-1 AND THE CORRESPONDING ANTI-PEPTIDE ANTIBODIES

[75] Inventors: John A. Schmidt, Mahwah; Joshua S. Boger; Ellen B. K. Bayne, both of Westfield, all of N.J.

[73] Assignee: Merck & Co., Inc., Rahway, N.J.

[21] Appl. No.: 208,954

[22] Filed: Jun. 17, 1988

Related U.S. Application Data

[62] Division of Ser. No. 782,847, Oct. 2, 1985, Pat. No. 4,772,685.

[51] Int. Cl.$^5$ .................. C07K 7/08; C07K 17/00
[52] U.S. Cl. ............................ 530/327; 530/300; 530/351; 530/806; 530/402; 530/403; 530/405; 530/810; 530/812; 424/85.1; 424/85.2; 424/85.8; 514/2; 514/14; 514/885
[58] Field of Search ........ 530/327, 345, 351, 403–406, 530/408, 409; 424/85.2, 85.91

[56] References Cited

U.S. PATENT DOCUMENTS 4,762,914 8/1988 Auron et al. ............ 530/351
4,766,069 8/1988 Auron et al. ............ 530/351
4,774,320 9/1988 Tayliabue et al. ........ 530/351

OTHER PUBLICATIONS

Rimsky et al., *LBC* 136, 1986, pp. 3304–3310.
Dinarello et al., *J. Immunol.*, 133, 9/84, p. 1332–13382.
Masliy et al., *PNAS* 84, 1987, pp. 4572–4576.
Regenmortel, *TiB* 11, 1986, pp. 36–39.
Shinnick et al., *Ann Res. Microbiol.* 1983, 37, pp. 425–446.
March et al., *Nature*, 315, 1985, pp. 641–647.

Primary Examiner—Garnette D. Draper
Attorney, Agent, or Firm—Jack L. Tribble; Hesna J. Pfeiffer

[57] ABSTRACT

Several distinct peptide regions of the secreted form of purified human interleukin-1 species pI 6.8 have been found to exhibit characteristics associated with highly immunogenic protein moieties and are used to produce specific anti-peptide antibodies. The antibodies raised against the individual peptides are specific for the peptide used for their production and for IL-1, pI 6.8. The individual antibodies bind to both the precursor of IL-1, pI 6.8 and the mature or extracellular IL-1, pI 6.8.

6 Claims, No Drawings

IMMUNOGENIC PEPTIDES OF HUMAN INTERLEUKIN-1 AND THE CORRESPONDING ANTI-PEPTIDE ANTIBODIES

This is a division of application Ser. No. 782,847, filed Oct. 2, 1985, now U.S. Pat. No. 4,772,685.

BACKGROUND OF THE INVENTION

The present invention relates to the specific peptides associated with distinct regions of human interleukin-1 (IL-1), species pI 6.8. This invention also relates to the production of antibodies which react monospecifically with the synthesized peptides and IL-1.

Specific antibodies capable of reacting monospecifically with human IL-1 have not been produced because purified IL-1 has not been available in amounts sufficient for antibody production and those preparations available in optimal quantity have not been sufficiently pure. Dinarello et al., Proc. Natl. Acad. Sci., (1977) 74: 4624–4627, initially produced antisera against human leukocytic pyrogen obtained from the culture fluid of human monocytes following the phagocytosis of heat-killed staphylococci. Cannon Dinarello, Science (1984) 227: 1247–1249, subsequently prepared antisera against human IL-1 with a molecular weight of 15,000 to 17,000. Neither of these antibody preparations differentiated between the identified species of human IL-1 or showed specificity for the human IL-1 molecule. However, antibodies with specificity for murine IL-1 have been produced by Mizel et al., J. Immunol. (1983) 131: 1834–1837, using IL-1 obtained from a murine macrophage cell line. Anti-mouse IL-1 antibodies showed only partial cross-reactivity with human IL-1 indicating a very limited similarity between murine IL-1 and the pI 6.8 species of human interleukin-1.

The ability to purify the major charged species, pI 6.8, of human interleukin-1 has allowed the amino acid sequence to be elucidated. The amino acid sequence corresponds exactly with the sequence deduced from a cloned cDNA for this species of human interleukin. The knowledge of the sequence of IL-1 has allowed the synthesis of various portions of the secreted form of IL-1. This in turn has permitted the production of monospecific antibodies which react with synthesized peptide regions of the human IL-1 species pI 6.8 molecule and the intact IL-1 molecule. The purification of human interleukin species pI 6.8 is disclosed in U.S. pat. appln. Ser. No. 769,231, filed Aug. 26, 1985, the disclosure of which is hereby incorporated by reference.

OBJECT OF THE INVENTION

It is, accordingly, an object of the present invention to provide peptide subunits of human IL-1 which will act as specific immunogens. Another object is to conjugate the specific peptides to a high molecular weight carrier protein. A further object is to produce monospecific antibodies against the synthesized peptides. Another object is to use the anti-peptide antibodies to detect IL-1 in cells, tissues and body fluids. These and other objects of the present invention will be apparent from the following description.

SUMMARY OF THE INVENTION

Several distinct peptide regions of the secreted form of purified human interleukin-1 species pI 6.8 have been found to exhibit characteristics associated with highly immunogenic protein moieties and are used to produce specific anti-peptide antibodies. The antibodies raised against the individual peptides are monospecific for the peptide used for their production and both the precursor IL-1, pI 6.8 and the mature or extracellular IL-1, pI 6.8.

DETAILED DESCRIPTION

The present invention relates to the specific peptides making up identified regions of human extracellular IL-1, pI 6.8, and the production of antibodies which react monospecifically with the peptides and IL-1.

The amino acid sequence of human IL-1, pI 6.8, has been deduced from cloned cDNA, Auron et al. (1984), Proc. Natl. Acad. Sci. 81: 7907–7911, and confirmed by amino acid sequence analysis of the purified protein, Cameron et al. (1985), J. Exp. Med. 162:790–801. The complete precursor molecule encoded for by the cDNA is 269 amino acids long. The extracellular, mature IL-1 begins at about Alanine (117), the amino terminus, and ends at about Serine (269), the likely carboxyl terminus as shown in the following table.

TABLE I

| | | | 120 | | | | | | | | | | 130 | |
|---|---|---|---|---|---|---|---|---|---|---|---|---|---|---|
| ALA | PRO | VAL | ARG | SER | LEU | ASN | CYS | THR | LEU | ARG | ASP | SER | GLN | GLN |
| | | | | | | | | 140 | | | | | | |
| LYS | SER | LEU | VAL | MET | SER | GLY | PRO | TYR | GLU | LEU | LYS | ALA | LEU | HIS |
| | | | 150 | | | | | | | | | | 160 | |
| LEU | GLN | GLY | GLN | ASP | MET | GLU | GLN | GLN | VAL | VAL | PHE | SER | MET | SER |
| | | | | | | | | 170 | | | | | | |
| PHE | VAL | GLN | GLY | GLU | GLU | SER | ASN | ASP | LYS | ILE | PRO | VAL | ALA | LEU |
| | | | 180 | | | | | | | | | | 190 | |
| GLY | LEU | LYS | GLU | LYS | ASN | LEU | TYR | LEU | SEP | CYS | VAL | LEU | LYS | ASP |
| | | | | | | | | 200 | | | | | | |
| ASP | LYS | PRO | THR | LEU | GLN | LEU | GLU | SER | VAL | ASP | PRO | LYS | ASN | TYR |
| | | | 210 | | | | | | | | | | 220 | |
| PRO | LYS | LYS | LYS | MET | GLU | LYS | ARG | PHE | VAL | PHE | ASN | LYS | ILE | GLU |
| | | | | | | | | 230 | | | | | | |
| ILE | ASN | ASN | LYS | LEU | GLU | PHE | GLU | SER | ALA | GLN | PHE | PRO | ASN | TRP |
| | | | 240 | | | | | | | | | | 250 | |
| TYR | ILE | SER | THR | SER | GLN | ALA | GLU | ASN | MET | PRO | VAL | PHE | LEU | GLY |
| | | | | | | | | 260 | | | | | | |
| GLY | THR | LYS | GLY | GLY | GLN | ASP | ILE | THR | ASP | PHE | THR | MET | GLN | PHE |
| VAL | SER | SER | | | | | | | | | | | | |

Several peptide segments are immunogens of the intact IL-1 and are shown in the following table:

TABLE II

| Sequence | Structure |
|---|---|
| 197-207 | GLN LEU GLU SER VAL ASP PRO LYS ASN TYR PRO |
| 202-215 | ASP PRO LYS ASN TYR PRO LYS LYS LYS MET GLU LYS ARG PHE |
| 188-198 | VAL LEU LYS ASP ASP LYS PRO THR LEU GLN LEU |
| 125-135 | THR LEU ARG ASP SER GLN GLN LYS SER LEU VAL |
| 164-174 | GLN GLY GLU GLU SER ASN ASP LYS ILE PRO VAL |
| 172-184 | ILE PRO VAL ALA LEU GLY LEU LYS GLU LYS ASN LEU TYR |
| 253-263 | THR LYS GLY GLY GLN ASP ILE THR ASP PHE THR |
| 150-164 | GLN ASP MET GLU GLN GLN VAL VAL PHE SER MET SER PHE VAL GLN |
| 117-128 | ALA PRO VAL ARG SER LEU ASN CYS THR LEU ARG ASP |
| 258-269 | ASP ILE THR ASP PHE THR MET GLN PHE VAL SER SER |

The first two sequences were combined into the resultant peptide beginning at about Glutamine (197) and continuing to about Phenylalanine (215). This peptide contains approximately 19 amino acids and is hereafter referred to as the primary internal peptide. The amino and carboxyl regions also function as immunogenic domains. Thus, a peptide starting at about Alanine (117) and continuing to about Aspartic acid (128), containing approximately the first 12 amino acids of the mature form of IL-1, pI 6.8, is referred to as the amino peptide. A third peptide, the carboxyl terminus, begining at about Aspartic acid (258) and continuing to about Serine (269) and containing approximately the last 12 amino acids of IL-1 and is hereafter referred to as the carboxyl peptide.

The peptides of the present invention may be synthesized using any suitable peptide synthesis technique, e.g., the solid phase peptide synthesis chemistry following the method of Merrifield, (1963). J. Am. Chem. Soc. 85: 2149-2154. As shown in Table III, cysteine is added to either the amino or the carboxyl terminus, preferably the amino terminus, of the primary internal and carboxyl peptides during synthesis to provide free sulfhydryl groups for coupling to an immunogenic carrier. The peptides can be used per se or in the form of their amides or acid-addition salts.

TABLE III

| | |
|---|---|
| 1. Amino peptide | 117<br>ALA PRO VAL ARG SER LEU ASN CYS<br>128<br>THR LEU ARG ASP |
| 2. Primary internal peptide | 197<br>CYS GLN LEU GLU SER VAL ASP PRO LYS ASN<br>215<br>TYR PRO LYS LYS LYS MET GLU LYS ARG PHE |
| 3. Carboxyl peptide | 258<br>CYS ARG ASP ILE THR ASP PHE THR MET GLN<br>269<br>PHE VAL SER SER |

The peptides are purified by preparative reverse phase high performance liquid chromatography (HPLC) and lyophilized. Purity is established by analytical reverse phase HPLC and composition was confirmed by amino acid analysis. The synthesized peptides are covalently coupled to a high molecular weight carrier protein, e.g., keyhole limpet hemocyanin or bovine serum albumin, preferably keyhole limpet hemocyanin (KLH), by the method of Kitagawa et al., (1981) Chem. Pharm. Bull., 29: 1130-1135. The covalently coupled peptides are hereafter referred to as peptide immunogens.

Heterologous polyclonal antibodies are raised by immunizing animals such as mice or mice with congenital autoimmune disease, rats, guinea pigs, rabbits, goats and horses, with rabbits being preferred, with an appropriate concentration of the specific peptide immunogen either with or without an immune adjuvant. Preimmune serum was collected prior to the first animal immunization. Each animal received between 50 μg and 300 μg of a single peptide immunogen associated with an acceptable immune adjuvant. Such acceptable adjuvants include, but are not limited to, Freund's complete, Freund's incomplete, alum-precipitate, water-in-oil emulsion containing *Corynebacterium parvum* and tRNA. The initial immunization consisted of the specific peptide immunogen in adjuvant at multiple intradermal sites. Each animal received booster injections consisting of the peptide immunogen in adjuvant until sufficient antibody levels were attained. This was usually achieved by injections at about 3 and about 5 weeks following the initial immunization. At about 10 days after the final injection, the animals are bled, the serum collected, aliquoted and stored at about $-20°$ C.

The concentration of monospecific peptide antibodies per unit volume of antiserum (titer) is determined using a solid phase binding assay employing either immobilized peptide or purified IL-1, species pI 6.8. Individual peptides or pure IL-1 are adsorbed to a polystyrene or polyvinyl chloride surface and reacted with varying dilutions of the specific antiserum. Each antisera raised against a single peptide reacted only with the immunizing peptide. All three sera raised against the individual peptides react with pure intact IL-1.

A solid phase immuno radio assay is used to show that the various anti-peptide antisera recognized the appropriate domain of the intact IL-1 molecule. Polyvinyl chloride surfaces are coated with various concentrations of IL-1 and contacted with the individual antiserum at various dilutions. The binding assay demonstrates that binding of the immune serum to a given peptide and IL-1 was blocked in a dose dependent manner by the relevant peptide whereas irrelevant peptides did not block. A relevant peptide is the peptide used to induce the specific antibody, e.g., if the amino peptide is used to produce anti-amino peptide antibody, the amino peptide is the relevant peptide. An irrelevant peptide is any peptide other than the one used to induce antibody synthesis.

The specificity of the anti-peptide antisera for intact IL-1 is tested by using the antisera for western blot analysis of crude concentrated supernatants derived from cultures of stimulated human peripheral blood mononuclear cells, Schmidt, (1984), J. Exp. Med. 160: 772-787. The crude concentrated culture supernatant liquids are analyzed by SDS polyacrylamide gel electrophoresis in 15% homogeneous gels under reducing conditions and transferred to nitrocellulose paper. The paper is reacted with anti-peptide antiserum and $^{125}I$ labeled protein A and examined by autoradiography. Antibodies to the three peptides recognize a single band in the crude supernatant liquid. The migration characteristics and band location correspond exactly with that of pure IL-1. Anti-peptide antisera also react with precursor IL-1, obtained from stimulated monocytes. Western blot analysis of monocyte lysates demonstrated that the antibodies to the peptides recognize a single band with a molecular weight of about 33,000 which corresponds to precursor IL-1.

Anti-peptide antiserum also immunoprecipitates human IL-1. The precursor or intracellular form of human IL-1 found in from disrupted, stimulated monocytes and is characterized by a molecular weight of about 33 kilodaltons (kd). The mature or extracellular form of human IL-1 is obtained from culture fluids of stimulated monocyts. The culture fluid in which the monocytes are grown contains $^{35}S$-methionine which is incorporated into both the precursor and mature form of IL-1. Agarose beads are coated with protein A and contacted with preimmune or immune serum. The bead-protein A-serum complex is reacted with precursor or mature human IL-1. The beads are washed and any precipitate dissolved and separated by SDS polyacrylamide gel electrophoresis. Immunoprecipitation of disrupted monocytes reveals a dominant $^{35}S$-labeled 33 kd band which is characteristic of precursor IL-1, pI 6.8. Immunoprecipitation of the culture supernatant reveals a 17 kd band which is characteristic of the mature extracellular form of human IL-1. Preimmune serum does not precipitate either form of IL-1.

Antisera raised against the individual peptide immunogens is used to detect the presence of IL-1, pI 6.8, in stimulated monocytes and in other cell types, such as epithelial cells, in tissue culture and tissue sections. This highly specific heterologous antisera allows the detection of not only the mature form of IL-1 but also the precursor molecule which is localized in the cytoplasm of cells, including monocytes and keratinocytes. Human mononuclear blood cells are collected and purified by discontinuous density gradient centrifugation. The mononuclear cells are cultured in a nutrient medium in the presence of stimulants, e.g., phytohemagglutinin and lipopolysaccharide. Cells cultured for about 4.5 hours are fixed according to the technique of McLean and Nakane, (1974), J. Histochem. Cytochem. 22: 1077-1083, and permeabilized by treatment with about 0.1% Triton X-100 in phosphate buffered saline. The cells are washed and contacted with either anti-peptide, or preimmune serum, obtained prior to immunization from the same animal as the anti-peptide antiserum, washed and stained with fluorescein isothiocyanate (FITC)-conjugated goat anti-rabbit IgG. The treated cells are observed microscopically for internal fluorescence. Stimulated cells which are identified as monocytes by their nuclear morphology when reacted with anti-peptide antiserum and stained with FITC-conjugated anti-rabbit IgG, show intense cytoplasmic fluorescence. Preincubation of anti-serum with the relevant peptide but not an irrelevent peptide abolishes the fluorescent staining. The anti-peptide antibodies does not react with lymphocytes or platelets present in the cell preparation. Preimmune serum does not bind to stimulated monocytes containing intracellular IL-1.

Anti-peptide antisera also binds to IL-1 producing cells in tissue sections obtained from individuals with acute or chronic inflammatory disease. Samples of inflamed gingiva from a person with severe periodontal disease were embedded and frozen sections prepared. The sections were reacted with anti-peptide antibodies, washed and stained with FITC-conjugated anti-rabbit IgG. Microscopic examination revealed IL-1 in keratinocytes. These cells showed no staining when treated with preimmune serum.

The availability of specific anti-peptide antibodies capable of reacting with known regions of a homogenously pure species of IL-1, pI 6.8, allows the detection of both intracellular, precursor IL-1 and extracellular, mature IL-1 by various immunocytochemical and serological assays. Since IL-1 containing cells, predominately monocytes, are associated with most acute and chronic inflammatory responses the ability to detect IL-1 containing cells by immunocytochemical techniques augments the effectiveness of diagnosing these disease states. Indeed, the rapid and specific detection of the number and types of IL-1-producing cells enhances the ability to diagnose pathologically similar disease states. The ability of anti-peptide antibodies to specifically immunoprecipitate human IL-1 expands the scope of immune assays for detecting the presence of cell free human IL-1. The anti-peptide antibodies allow the detection of antigen by radioimmune assay (RIA) in biological fluids, e.g., blood, serum, lymph or urine, and in extracts prepared from human cells and tissues. Conversely, the purified IL-1 and the synthesized peptides are used in radioimmune assays to detect anti-IL-1 antibodies which may be involved in certain types of autoimmune diseases. A RIA can detect the presence of IL-1 in body fluids, such as serum or plasma.

The following examples illustrate the present invention without, however, limiting the same thereto.

EXAMPLE 1

Peptide Synthesis and Purification

The three peptides shown in Table III were synthesized using t-Boc chemistry and a SAM TWO Peptide Synthesizer (Biosearch, Inc.). The synthesis of the amino peptide and the primary internal peptide was performed on 4-methylbenzhydrylamine resin in order to obtain the C-terminal amide. The carboxyl peptide was synthesized on the standard Merrifield resin. The synthesis procedure is described in detail in the SAM TWO Peptide Synthesizer Operator's Manual (Biosearch, 1985). Cleavage of the synthesized peptide from the appropriate resin was accomplished by treatment with hydrogen fluoride in a Biosearch hydrogen fluoride apparatus following procedures outlined in the SAM TWO Operator's Manual. The peptides were purified by high performance liquid chromatograph using an alkyl silane substrate with 18 carbon atoms as described in the SAM TWO Operator's Manual. Purity of the individual peptides was assessed by reversed phase high performance liquid chromatography (HPLC) and by amino acid analysis, again following set procedures as described in the SAM TWO Owner's Manual. The synthesized peptides were coupled to Keyhole Limpet Hemocyanin (KLH) by the method of Kitagawa et al., (1981), Chem. Pharm. Bull., 29: 1130–1135.

EXAMPLE 2

Production of Anti-peptide Antibodies

Three groups of New Zealand White rabbits (1.5 kg) were bled and then immunized with 200 μg of each peptide-KLH conjugate, peptide immunogen, in complete Freund's adjuvant at multiple intradermal sites. Repeat injections of conjugate in incomplete Freund's adjuvant were given three and five weeks later at multiple subcutaneous sites. Ten days after the last immunization, the rabbits were bled and the serum was aliquoted and frozen at −20° C.

EXAMPLE 3

Determination of Antibody Titer Using a Solid Phase Immuno Radio Assay

The titer of the antisera raised to the respective peptide-KLH conjugates was determined by using a solid phase binding assay employing either immobilized peptide or pure IL-1 (pI 6.8). Peptide (500 ng/ml) or pure IL-1 (500 ng/ml) was allowed to bind to flexible polyvinyl/chloride microtiter wells (Dynatech) in phosphate buffered saline (PBS), pH 7.2, overnight at 4° C. The following day, the wells were washed in PBS containing 1.5% horse serum (HS) and then blocked with PBS containing 10% HS for two hours at room temperature. Antiserum diluted in PBS/1.5% HS was then applied in 100 μl volumes and allowed to stand for two hours at room temperature. After washing three times with PBS/1.5% HB, 100 μl of $^{125}$I labeled protein A (100,000 cpm/well; 1×10$^8$ cpm/mg) was added to each well and incubated for two hours at room temperature. After washing five times the plates were dried. The bottoms of the wells were removed with a hot wire and counted in a gamma counter. The following results were obtained.

| Serum Dilution | Peptide | | IL-1 | |
|---|---|---|---|---|
| | Immune Serum | Preimmune Serum | Immune Serum | Preimmune Serum |
| | CPM × 10$^{-3}$ | | | |
| 10$^{-1}$ | 24 | 0.8 | 20 | 1 |
| 10$^{-2}$ | 26 | 0.5 | 15 | 0.8 |
| 10$^{-3}$ | 15 | 0.3 | 8 | 0.5 |
| 10$^{-4}$ | 6 | 0.3 | 3 | 0.3 |

These results show that sera obtained from a rabbit immunized with the amino peptide immunogen bound not only to the amino peptide to which it was raised but also to intact IL-1 in a dose dependent manner. The preimmune serum did not bind to either the relevant peptide or intact IL-1. Identical results were seen with sera obtained from rabbits immunized with the primary internal peptide and the carboxyl peptide. The titers of the antisera are representative of those obtained in rabbits immunized with the various peptide immunogens.

EXAMPLE 4

Determination of Anti-peptide Antisera Binding to the Appropriate Domain of Intact IL-1

Competitive solid-phase binding experiments demonstrate that the various anti-peptide antisera recognized the appropriate domain of the intact IL-1 molecule. A single, sub-saturating dilution of antiserum raised to the amino peptide immunogen was preincubated with increasing amounts of relevant peptide, amino peptide, or irrelevant peptide, primary internal peptide, prior to assay on wells coated with the amino peptide or pure IL-1.

| Concentration of Soluble Peptide (ng/ml) | Plate Coated With Peptide | | Plate Coated With IL-1 | |
|---|---|---|---|---|
| | Anti-serum pre-incubated with | | Anti-serum pre-incubated with | |
| | Relevant Peptide | Irrelevant Peptide | Relevant Peptide | Irrelevant Peptide |
| | CPM × 10$^{-3}$ | | | |
| 0 | 28 | 22 | 12 | 9 |
| 10$^1$ | 23 | 23 | 8 | 10 |
| 10$^2$ | 17 | 23 | 2 | 10 |
| 10$^3$ | 8 | 23 | 1 | 10 |
| 10$^4$ | 2 | 23 | 0.5 | 10 |

The binding of the immune serum to peptide and IL-1 was blocked in a dose dependent manner by relevant peptide whereas irrelevant peptide did not block in either case. Similar results were obtained with antisera to the primary internal peptide and the carboxylpeptide.

EXAMPLE 5

Enzyme-Linked Immunosorbent Assay for Intact IL-1

Polystyrene microtiter wells (Dynatech) were coated with various concentrations of IL-1 ranging from 0.4 to 50 μg/ml in 0.015M sodium carbonate buffer, pH 9.6, overnight at 4° C. The following day, the wells were washed three times with PBS/0.05% Tween and then blocked with 1% gelatin/PBS/Tween for 1 hour at room temperature. Serial log dilutions of antiserum to the primary internal peptide in PBS/Tween, were applied in 100 μl volumes to the wells and incubated at room temperature for one hour. After washing three times, 100 μl of affinity purified goat anti-rabbit IgG-horseradish peroxidase conjugate (BioRad), diluted 1:1000 in PBS/Tween, was added to the wells and incubated for one hour at room temperature. After washing three times, 100 μl of substrate (2.2'-azino-di-(3-ethylbenzthiazoline sulfonate) ABTS), Kirkegaard and Perry Laboratories) was added, incubated 10 minutes, and quenched with 100 μl of 5% sodium dodecylsulfate SDS. Optical density was then read with a multiscan plate reader (Titertek) at 405 nm. The following results were obtained.

| Serum Dilution | IL-1 Concentration (ng/well) | | | |
|---|---|---|---|---|
| | 0.4 | 2 | 10 | 50 |
| | Optical Density | | | |
| $10^{-1}$ | 0.40 | 0.93 | 1.10 | 1.20 |
| $10^{-2}$ | 0.21 | 0.84 | 1.09 | 1.18 |
| $10^{-3}$ | 0.17 | 0.53 | 0.95 | 1.09 |
| $10^{-4}$ | 0.10 | 0.23 | 0.55 | 0.75 |
| $10^{-5}$ | 0.09 | 0.12 | 0.23 | 0.35 |
| $10^{-6}$ | 0.08 | 0.09 | 0.15 | 0.27 |

The amount of chromophore obtained with each concentration of immune serum increased as the amount of IL-1 used to coat the wells was increased. No appreciable absorbance was obtained with preimmune serum even when the highest concentrations of IL-1 and serum were used.

EXAMPLE 6

Determination of Specificity of Anti-peptide Antisera for Intact IL-1

In order to test the specificity of the anti-peptide antisera for intact IL-1 (pI 6.8), the immune and preimmune sera were used in "western" analysis of crude concentrated culture supernatant and monocyte lysates. In these experiments, the supernatant liquids derived from human mononuclear cells stimulated with both phytohemagglutinin and lipopolysaccharide were concentrated 100-fold and analyzed by SDS PAGE in 15% homogeneous gels under reducing conditions. The gels were preequilibrated in transfer buffer (20 mM Tris, 1% glycine, 0.1% SDS, pH 8.6) for 20 minutes at room temperature and then rested upon a sheet of presoaked filter paper (3 mm, Whatman). The sandwich was completed by applying pre-soaked sheets of nitrocellulose and filter paper to the exposed surface of the gel. Electrophoretic transfer to the nitrocellulose was performed in a BioRad transblot apparatus at 4° C overnight at a constant voltage of 30 volts. Completeness of transfer was demonstrated afterwards by silver staining of the polyacrylamide gel. The nitrocellulose sheet was washed three times in PBS, blocked in 0.5% gelatin/PBS for one hour, and washed with 0.1% gelatin/PBS. The nitrocellulose strips were then incubated in a 1:100 dilution of antiserum in 20 mM Tris buffer pH 8.6 for one hour with gentle agitation. Afterwards, the strips were washed three times in Tris buffer (10 minutes each wash) and then incubated in $^{125}I$ protein A (200,000 cpm/ml; 25 ml; $1 \times 10^8$ cpm/mg) for one hour. Following washing six times in Tris buffer the sheets were air dried and exposed to Kodak X-0-MAT film for four days. Precursor IL-1 was obtained from adherent mononuclear cells stimulated with lipopolysaccharide and phytohemagglutinin, washed with serum free medium, scraped into Hanks balanced saline containing 5 mM N-ethylmaleimide, 2 mM phenylmethylsulfonyl fluoride and 2 mM EDTA, pelleted and resuspended in β-mercaptoethanol-containing sample buffer for SDS-PAGE. Samples were handled as described above.

Antiserum to the amino peptide immunogen recognized a single band in crude concentrated culture supernatants. Western analysis of pure IL-1 showed that the band identified in the crude material had the same mobility as IL-1.

The use of the anti-peptide antisera in western analyses of pure IL-1 and crude concentrated culture supernatant gave the following results. All three of the antisera bound pure IL-1, while no bands were observed with preimmune serum or $^{125}I$ protein A alone. All three antisera recognized a major band in crude concentrated culture supernatant having a mobility identical to pure IL-1 with a molecular weight of 17 kd. Once again, no bands were seen with either pooled preimmune serum or $^{125}I$ protein A alone. Silver staining of crude concentrated culture supernatant showed it to be very complex with many distinct protein species. Culture medium in which peripheral blood mononuclear cells were only briefly suspended was negative by this analysis. Western analysis of monocyte lysates gave the following results. All the antiserum recognized a single 31–33 kd band consistent with the size of the IL-1, pI 6.8 precursor. Treatment with preimmune serum and $^{125}I$-labeled protein A or $^{125}I$-labeled protein A alone showed no binding. Identical results obtained in experiments using anti-primary internal peptide further indicated that the 33 kd protein shaes more than one antigenic determinant with secreted IL-1.

EXAMPLE 7

Immunoprecipitation of Precursor and Mature Human IL-1 by Anti-peptide Antibodies 2 mg of protein A-coated Sepharose beads (Pharmacia) were swollen in buffer (500 mM NaCl, 10 mM Tris, 0.1% NP-40, pH 8.0) and then incubated with 6–10 μl of preimmune or anti-primary internal peptide antiserum overnight at 4° C on a rotary mixing apparatus. The beads were then washed three times in buffer, resuspended in 300 μl of buffer, and incubated with 100–300 μl of monocyte detergent lysate or 1.0–1.5 ml of crude monocyte culture supernatant for two hours at four degrees on a rotary mixer. The monocyte cultures from which the lysates and supernatants were derived had been previously stimulated, or not, with lipopolysaccharide in the presence of $^{35}$-methionine (Amersham; 1470 Ci/mmol; 87 μCi/2 ml culture medium). Subsequently, the beads were spun and washed three times with buffer. The precipitates were then dissolved in 50 μl of Laemmli sample buffer, boiled for five minutes, and electrophoresed on a 15% SDS gel. The gels were dried and autoradiography was performed.

Immunoprecipitation of lysates of LPS-stimulated monocytes with beads coated with immune serum revealed a dominant $^{35}$S-labeled 33 kd band, consistent with the known size of the IL-1 precursor. The band was not found with beads coated with preimmune serum, in the case of unstimulated monocytes, or if the protein A beads coated with immune serum were pretreated with excess amounts of primary internal peptide or intact IL-1 (pI 6.8). Immunoprecipitation of the culture supernatants revealed a 17 kd band with the same properties mentioned above, consistent with the known size of the mature, secreted form of IL-1.

EXAMPLE 8

Detection of IL-1 Within Human Mononuclear Cells Using Anti-peptide Antisera Human mononuclear cells were isolated from the blood of normal volunteers by Ficoll-Hypaque (Pharmacia) discontinuous density gradients. The cells obtained were suspended in RPMI medium containing 1% fetal calf serum (GIBCO Laboratories) 20 mM HEPES, 100 μ/ml penicillin and 100 μg/ml streptomycin. Two-$3 \times 10^6$ cells were seeded into 35 mm culture plates containing circular glass coverslips, and incubated at 37° C in 5% $CO_2$/air for 4–24 hour periods of time. For experiments on stimulated monocytes and lymphocytes 1 μg/ml lipopolysaccharide (LPS) from *E. coli* 055.B5 (Sigma Chemical Company) and 5 μg/ml phytohemagglutin (PHA) (Sigma) were added to the culture medium.

For immunofluorescent analyses, cell cultures were fixed for 20–25 minutes at room temperature in 2% paraformaldehyde and then permeabilized by treatment with 0.1% Triton X-100 in PBS for 5 minutes at 4° C or acetone for 30 minutes at −20° C, and washed well with PBS. Such preparations, if stored in PBS at 4° C, were stable for several weeks. Prior to staining, the cultures were briefly treated with Tris-HCl 0.1M pH 7.8 and then incubated for 20 minutes with 0.1M phosphate buffer (pH 7.8) containing 5% nonfat dry milk, 0.1% BSA and 0.04% sodium azide in order to minimize nonspecific antibody binding. After several washes with Tris-HCl, the cultures were incubated with anti-peptide antisera or preimmune sera diluted 50–100X, washed and stained with a 1:100 dilution of fluorescein isothiocyanate (FITC)-conjugated goat anti-rabbit IgG (Cappel Laboratories). All antibodies were diluted in 0.1M phosphate buffer containing 0.1% BSA, 0.04% azide and 0.1% nonfat dry milk and centrifuged to remove particulates prior to use. Specimens were viewed on a Zeiss fluorescence microscope equipped for epiillumination with a narrow band selective filter combination for FITC. Micrographs were prepared using Kodak Tri-X film developed at 20° C for 18 minutes with acufine developer (Acufine Inc.).

Cells which had been cultured for 4.5 hours in the presence of LPS and PHA were reacted with antiserum raised against the amino peptide immunogen and an FITC-conjugated goat anti-rabbit IgG. Intense cytoplasmic fluorescence was observed in cells which were identified by nuclear morphology as monocytes. No staining was seen in lymphocytes or platelets present in the same preparations. Control experiments demonstrated that when preimmune serum, or anti-KLH serum was substituted for the amino peptide antiserum, no fluorescent staining was obtained. Antiserum to the primary internal peptide of IL-1, however, produced staining which was indistinguishable from that seen with the antiserum to the amino peptide.

In view of the observed fluorescent staining of stimulated monocytes, it was also of interest to examine unstimulated cells and determine whether they too contained immunocytochemically detectable antigen. Accordingly, mononuclear cells were isolated as before and suspended in LPS and PHA-containing culture medium. A portion of the cell suspension was then immediately placed on ice and the cells pelleted onto slides using a cytofuge. The remaining cells were allowed to adhere to glass coverslips and incubated at 37° C (in the presence of LPS and PHA) for four hours. When such preparations were fixed, permeabilized and treated with immune serum followed by FITC-conjugated second antibody, the stimulated monocytes, as expected, showed intense fluorescence, while cells which had been suspended in the same medium but then immediately cytofuged and fixed showed no fluorescence. Thus, immunocytochemically detectable IL-1 is not present constitutively within monocytes, but rather must be induced by appropriate stimuli. To further test the specificity of the staining reaction, antiserum was preincubated with either the relevant peptide, or with irrelevant peptide or protein, and then used to stain cultures of stimulated mononuclear cells. Diluted antiserum (1:100) was preincubated with: (1) relevant IL-1 peptide (unconjugated; 50 μg/ml), (2) irrelevant IL-1 peptide (unconjugated; 50 μg/ml), or (3) ovalbumin (100 μg/ml) for 2.5 hours at room temperature. The serum was then used for indirect immunofluorescent staining as described above. The ability of immune serum to stain monocytes was completely abolished by preincubation with 10 μg/ml or 50 μg/ml of relevant peptide. Preincubation of the antiserum with the same concentrations of irrelevant peptide or with 100 μg/ml of ovalbumin had no effect on immunofluorescence. These findings indicate that the observed indirect immunofluorescent staining is a result of specific antibody interactions with appropriate IL-1 determinants.

EXAMPLE 9

Detection of IL-1 in Human Tissue Sections Using Anti-peptide Antisera

Samples of inflamed gingiva were obtained from a patient with severe periodontal disease, embedded in O.C.T. compound, frozen at −20° C, and sectioned on a cryotome. Ten micron sections were transferred to slides and air dried at room temperature. The tissue sections were treated with 2% paraformaldehyde at room temperature for 25 minutes followed by 0.1% Triton-X-100 in phosphate buffered saline for 5 minutes at 4° C. Indirect immunofluorescent staining was carried out as described in Example 7. The antiserum which was raised against monocyte IL-1 reacted specifically with IL-1 in epithelial cells as shown by intense cytoplasmic fluorescence. Immunofluorescent staining was abolished by pretreatment of the antiserum with the relevant peptide but not irrelevant peptides. Preimmune serum did not complex with the intracellular IL-1.

What is claimed is:

1. A peptide having the amino acid sequence ALA PRO VAL ARG SER LEU ASN CYS THR LEU ARG ASP or the amide or acid addition salts thereof.

2. A peptide immunogen comprising the peptide of claim 1 conjugated to a high molecular weight carrier protein.

3. The peptide immunogen of claim 2 wherein the high molecular weight carrier protein is keyhole limpet hemocyanin.

4. A peptide having the amino acid sequence CYS ARG ASP ILE THR ASP PHE THR MET GLN PHE VAL SER SER or the amide or acid addition salts thereof.

5. A peptide immunogen comprising the peptide of claim 4 conjugated to a high molecular weight carrier protein.

6. The peptide immunogen of claim 5 wherein the high molecular weight carrier protein is keyhole limpet hemocyanin.

* * * * *